(12) United States Patent
Zhang et al.

(10) Patent No.: US 10,405,954 B2
(45) Date of Patent: Sep. 10, 2019

(54) COMPACT ORAL HYGIENE DEVICE

(71) Applicants: Winston Zhang, Irvine, CA (US); Grace Yu Zhang, Irvine, CA (US)

(72) Inventors: Winston Zhang, Irvine, CA (US); Grace Yu Zhang, Irvine, CA (US)

( * ) Notice: Subject to any disclaimer, the term of this patent is extended or adjusted under 35 U.S.C. 154(b) by 0 days.

(21) Appl. No.: 16/121,761

(22) Filed: Sep. 5, 2018

(65) Prior Publication Data

US 2019/0008618 A1 Jan. 10, 2019

(51) Int. Cl.
| | |
|---|---|
| *A61C 17/02* | (2006.01) |
| *A61Q 11/00* | (2006.01) |
| *A61C 17/22* | (2006.01) |
| *A46B 5/00* | (2006.01) |
| *A61C 17/032* | (2006.01) |
| *A46B 9/04* | (2006.01) |
| *A46B 11/06* | (2006.01) |
| *A61C 1/00* | (2006.01) |

(52) U.S. Cl.
CPC .......... *A61C 17/032* (2019.05); *A46B 5/0095* (2013.01); *A46B 9/04* (2013.01); *A46B 11/06* (2013.01); *A61C 17/0202* (2013.01); *A61C 17/0205* (2013.01); *A61C 17/227* (2013.01); *A61Q 11/00* (2013.01); *A46B 2200/1066* (2013.01); *A61C 1/0092* (2013.01)

(58) Field of Classification Search
CPC ............ A61C 17/0214; A61C 17/0202; A61C 17/0205; A61C 17/227; A61C 1/0092; A46B 11/06; A46B 9/04; A46B 5/0095; A46B 2200/1066; A61Q 11/00
See application file for complete search history.

(56) References Cited

U.S. PATENT DOCUMENTS

| | | | | |
|---|---|---|---|---|
| 2004/0209222 | A1* | 10/2004 | Snyder | ............... A61C 17/02 433/80 |
| 2014/0272782 | A1* | 9/2014 | Luettgen | ............... A61H 13/005 433/80 |
| 2015/0147717 | A1* | 5/2015 | Taylor | ............... A61C 17/0205 433/80 |
| 2017/0318951 | A1* | 11/2017 | Taghvai | ............... A46B 11/001 |

* cited by examiner

*Primary Examiner* — Quang D Thanh

(57) ABSTRACT

A compact oral hygiene device includes a unique mini constant jet pump which integrated with a motor, has three diaphragm chambers, draws the fluid from a reservoir and propels fluid out from a buffer room to tips at constant pulseless, high efficiencies and low noise; and a plurality of exchangeable tips cleanses teeth and the interdental area.

4 Claims, 5 Drawing Sheets

COMPACT ORAL HYGIENE DEVICE

CROSS-REFERENCE TO RELATED APPLICATIONS

This application is related to the U.S. patent application Ser. No. 13/945,036, filed Jul. 18, 2013 titled "Oral Hygiene System" and its Continuation-In-Part U.S. Pat. No. 10,064,710. The disclosures of which are hereby incorporated herein in their entireties.

FIELD OF INVENTION

The field of the invention is oral hygiene devices.

BACKGROUND OF THE INVENTION

Various water irrigators have been in the prior art of records, or application's inventions. They are using pulsed water generated by a piston pump with syringe style nozzles for oral hygiene. For example, the Water Pik claims that "The production of 1,200 pulsations per minute was found to be a key component of effectiveness."

As recognized by the present inventor that the pulsed water lessens the force. F=ma, Half of times the force of the pulsed water equals zero because a=0.

An Oral Hygiene has to be done daily. Therefore, the inventor intents to provide a complete oral hygiene system which includes in house, traveling and in office models and that concept was disclosed in the patent application Ser. No. 13/945,036. The oral hygiene in house model is disclosed in the Pat. No. 10,064,710. This application is disclosing oral hygiene traveling and in office models and the concept is completely realized.

The present invention overcomes and satisfies the shortcomings, limitations or disadvantages of all water irrigators in the prior art of records, or application's inventions.

CROSS REFERENCE

U.S. Patent Documents

| | | |
|---|---|---|
| 8,449,295 | May 28, 2013 | Hegemann |
| 9,597,161 | Mar. 21, 2017 | Luettgen et al. |
| 20170209234 | Jul. 27, 2017 | Senff et al. |
| 9,775,692 | Oct. 3, 2017 | Thomas et al. |
| 9,980,793 | May 29, 2018 | Wagner et al. |
| 9,980,794 | May 29, 2018 | Snyder et al. |

SUMMARY OF THE INVENTION

The present invention, compact oral hygiene device, may comprise a body, a reservoir and an oral hygiene-ware. The body is housing a battery, a mini constant jet pump and a control circuitry. The reservoir is detachable to the body and store the fluid.

The mini constant jet pump is a unique mini pump for the compact oral hygiene device; I named it a "constant jet", a pulseless pump. The mini constant jet pump integrated with a motor and comprises three diaphragm chambers. The mini constant jet pump further comprises a lever with three arms mounted at the bottoms of those three chambers. A center pole of the lever eccentrically inserts into a rotating arm of the motor. The layer is not rotating during the motor running but the lever's arms oscillating at one of the arms is going down and two other arms are going up. The going down arm pushes the diaphragm down and propels fluid out from the chamber. The going up arms release the pressure on the diaphragms, the diaphragms go back to the original shape and the fluid is drawn from the reservoir into the chambers. This circulation repeats during the motor running. The mini constant jet pump further comprises a buffer room. Three outlets of the chambers are fluidly connected to the buffer room. The buffer room has to be specially designed based on the volumes of fluid from three outlets of the chambers, the outlet size of the buffer room as well as an expected pressure. The outlet of the buffer room is the mini constant jet pump's outlet. The mini constant jet pump draws fluid from the reservoir three times during one circle of the motor rotating. The fluid propels out from the mini constant jet pump as a constant pulseless fluid jet. The mini constant jet pump can be very compact and provide pressure of approximately 60-90 psi. The diameter of the mini constant jet pump can be about 1 inch and the length of the mini constant jet pump can be about 2.5 inch. The mini constant jet pump is very low noise at about 55 dB. The motor is driven by a DC 2.4-6V power source such as batteries, rechargeable batteries and USB cable. The mini constant jet pump is very high efficacy up to 97%.

The oral hygiene-ware connects to the body's outlet. The oral hygiene-ware may have soft hose, handle and tips.

A plurality of exchangeable tips could utilize constant pulseless water jet's blasting, penetrating and cleansing features. For example, A Waterjet Brush tip comprises a toothbrush head at the hygiene end of the tip; the toothbrush head comprises two nozzles at the crosses of the front and the side edges. A conduit fluidly connects an inlet to the nozzles. The nozzles are parallel to the bristles and 1-1.5 mm shorter than the bristles. USC studied that water stream touches effectively remove 99.9% plaque in a laboratory by a third party. The nozzles with a stable supported by the bristles could stay to blast one spot remove plaque 99.9% such as blast white spot lesion to stop tooth decay process. User could also use the nozzles penetrating to dilute the acid for avoid lesion. The Waterjet Brush tip can do brushing and water jet cleansing simultaneously.

A Swirl Water jet tip having a pipe with a male external thread and a cap with a female internal thread and a pinhole centrally located at the top of the cap disposed at the hygiene end being arranged such that said pipe includes a mechanism that divides single flow into two separated flows that twist with respect to each other. The tip could eject fluid out to forms a umbrella shaped high speed rotating water wheel, the umbrella shaped high speed rotating water wheel could open user's periodontal pocket to wash out plaque, meanwhile the umbrella shaped high speed rotating water wheel generates a low pressure zone by the constant pulseless fluid flow, the plaques deep inside of user's periodontal pocket could be sucked out; the Swirl Water jet could also eject out fluid stream to cleanse user's interdental area.

A Jet Goupillon tip is unique for cleansing aligners, retainers, dentures and artificial teeth for orthodontic and dental treatment patients.

One embodiment of the compact oral hygiene device is a portable model; the tip connects the body thought a handle with hose. Another embodiment is a pocket model; the tip connects to body's outlet directly.

Various objects, features, aspects and advantages of the present invention will become more apparent from the following detailed description of preferred embodiments of the invention, along with the accompanying drawings in which like numerals represent like components.

BRIEF DESCRIPTION OF THE DRAWINGS

FIG. 1-1 is a perspective view of the body of the embodiment of the portable model of the compact oral hygiene device.

FIG. 3-1 is a schematic view of the mini constant jet pump.

FIG. 7-1 is a cross-sectional view showing the front section of the Jet Goupillon tip.

DESCRIPTION OF THE PREFERRED EMBODIMENTS

Figure 1:
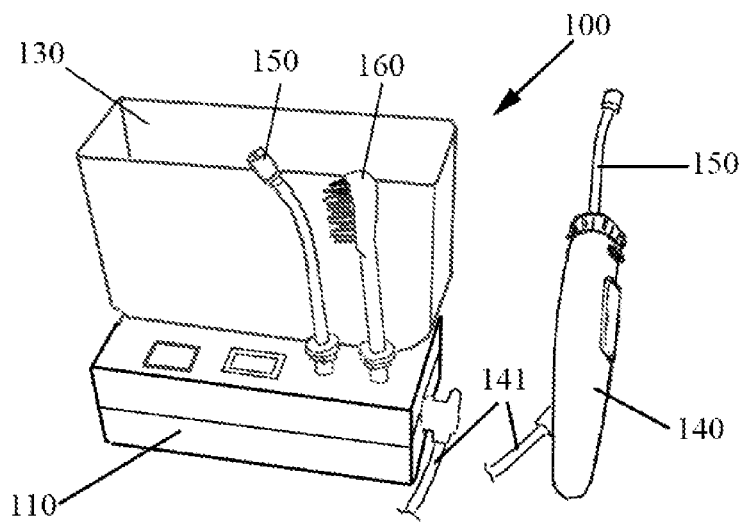
FIG. 1 is a perspective view of an embodiment of the portable model of the compact oral hygiene device.
Figure 1:
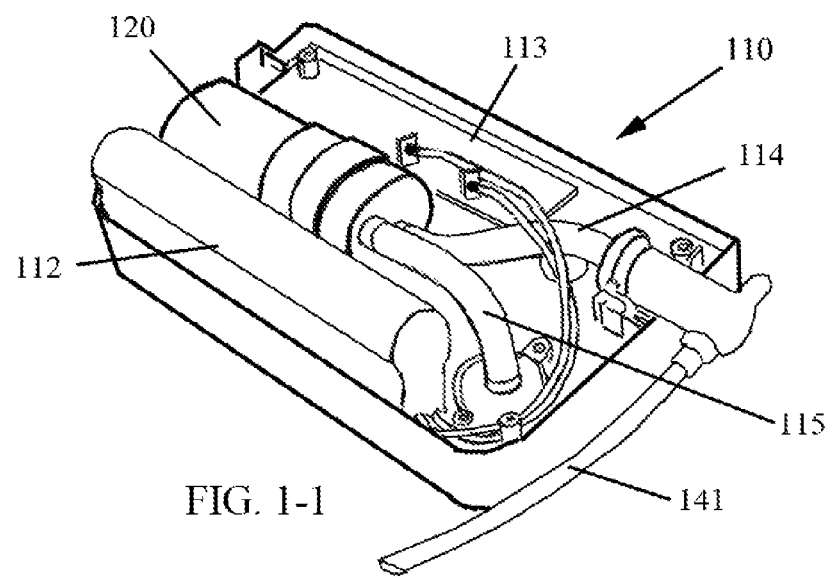

With reference to FIG. 1, an embodiment of a compact oral hygiene device 100 generally comprises a body 110, a reservoir 130, tips 150, 160 and a handle 140.

With reference to FIG. 1-1, the body 110 is housing a rechargeable battery 112, a mini constant jet pump 120 and control circuitry 113.

Figure 3:
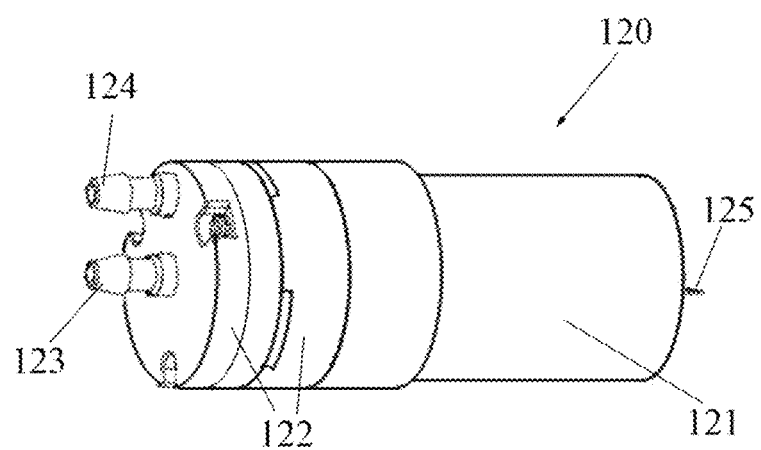
FIG. 3 is a perspective view of the mini constant jet pump.
Figures 1, 3:
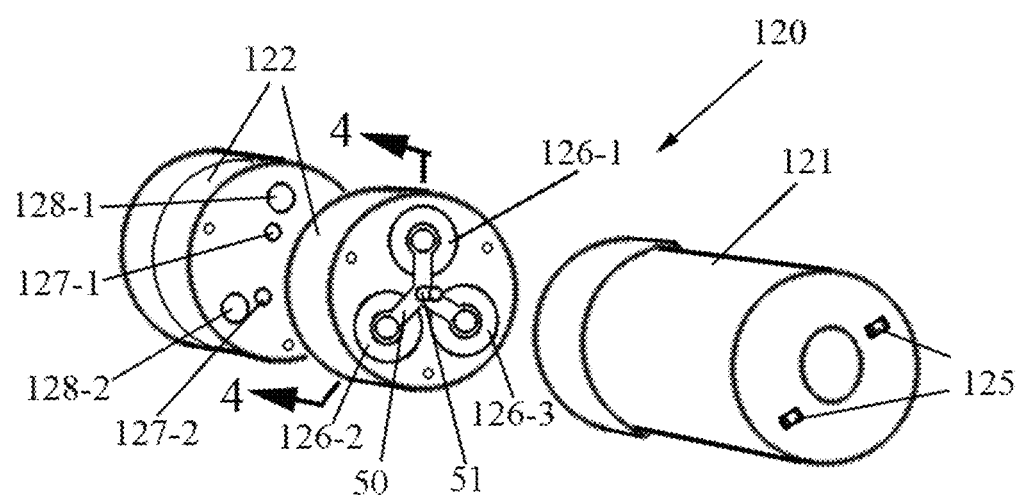

The mini constant jet pump 120 is a unique mini pump for the compact oral hygiene device 100. The mini constant jet pump 120 is integrated with a motor 121 as show in FIGS. 3, 3-1 and 4. The mini constant jet pump 120 comprises three diaphragm chambers 126-1, 126-2 and 126-3. The mini constant jet pump 120 further comprises a lever 50 with three arms mounted at the bottoms of those three chambers 126-1, 126-2 and 126-3. The lever 50 comprises a center pole 51 which eccentrically inserts into a rotating arm 60. The rotating arm 60 is mounted at the axis of the motor 121 and rotating by the motor 121. During the motor 121 rotating, the lever 50 did not rotating but the three arms of the lever 50 are oscillating at one going down with two others going up caused the volume of the chambers 126-1, 126-2 and 126-3 are decreased and increased.

Figure 4:
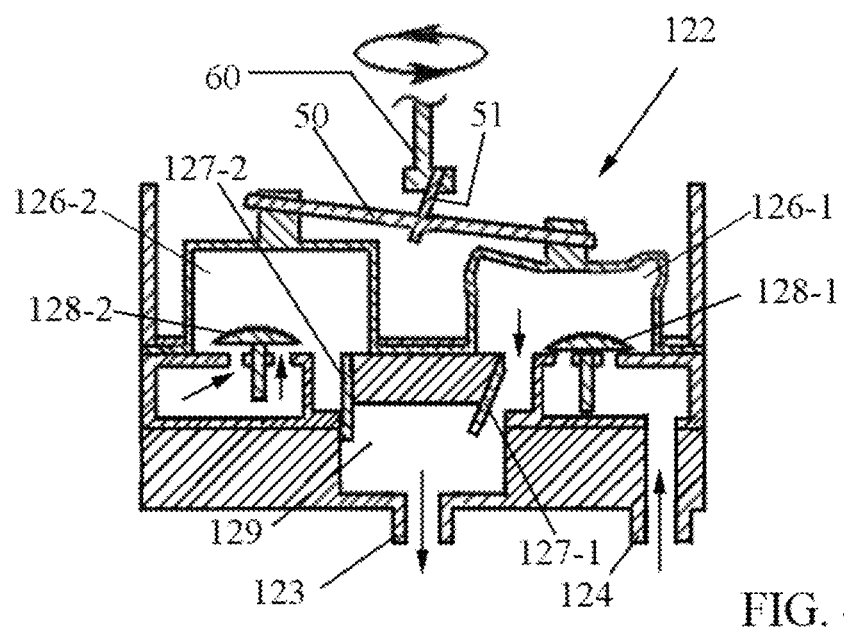
FIG. 4 is a cross-sectional view showing the fluid flow of the mini constant jet pump.

With reference to FIG. 4, the rotating arm 60 is rotated with the motor 121, the center pole 51 of the lever 50 eccentrically inserts into the rotating arm 60 caused one arm of the lever 50 is going down; and pressing the diaphragm of the chamber 126-1 down and the volume of the chamber 126-1 is decreased; the fluid in the chamber 126-1 is propelled out from the outlet check valve 127-1 into the buffer room 129. And the inlet check valve 128-1 is closed. Meanwhile, other arms of the lever 50 are going up; and pressure released caused diaphragm of the chamber 126-2 goes back to the original shape and the volume of the chamber 126-2 is increased; the inlet check valve 128-2 is open and fluid is drawn into the chamber 126-2. And outlet check valve 127-2 is closed.

The above circulation repeats during the motor 121 running. The mini constant jet pump 120 draws fluid three times from the reservoir 130 through an inlet 124 into each chamber 126-1, 126-2 and 126-3 during one circle of the motor 121 rotating. Meanwhile, the fluid propels out from an outlet 123 of the mini constant jet pump 120 as a constant pulseless fluid jet.

With reference to FIG. 1 and FIG. 1-1, the mini constant jet pump 120 draws the fluid from the reservoir 130 through an inlet hose 115 then ejects out a constant pulseless fluid through an outlet hose 114. Then fluid flows into the handle 140 through a soft hose 141 and ejects out from a tip 150 into user's mouth for oral hygiene. The body 110 can be stored inside of the reservoir 130 after the usage.

Figure 2:
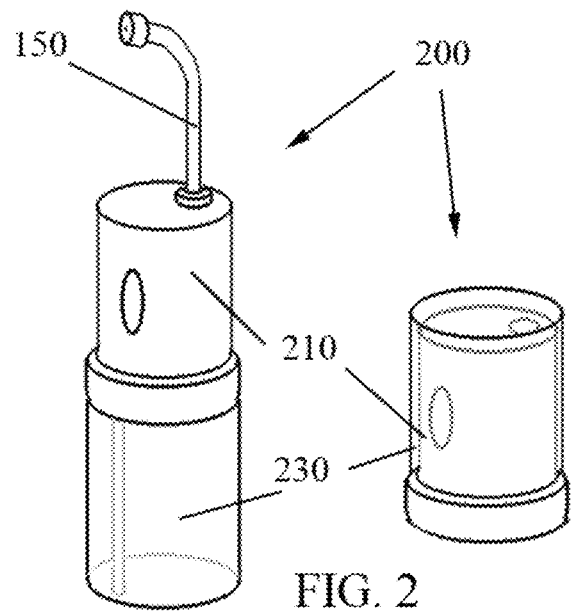
FIG. 2 is a perspective view of an embodiment of the pocket model of the compact oral hygiene device.

With reference to FIG. 2, another embodiment of a compact oral hygiene device 200 generally comprises a body 210, a reservoir 230, tips 150 and 160. The body 210 is housing a mini constant jet Pump 120, a 2.4-3V battery and a circuitry. The tip 150 directly connects to the outlet of the body 210. The body 210 can be stored into the reservoir 230 after the usage.

Figure 6:
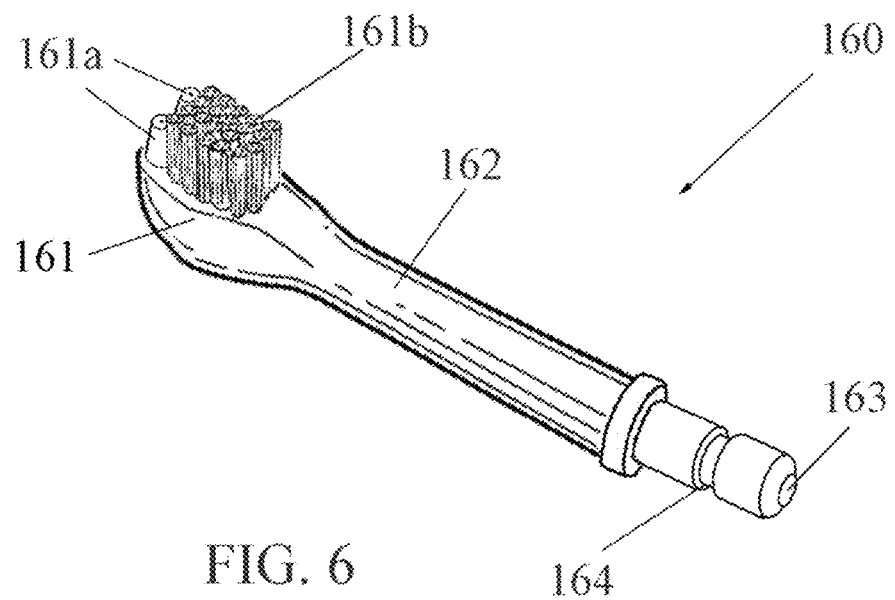
FIG. 6 is a schematic showing an embodiment of tip, a Waterjet Brush tip.

For general users, a Waterjet Brush tip is recommended. With reference to FIG. 6, the Waterjet Brush tip 160 comprises a toothbrush head 161 at the hygiene end of the tip, a tip body 162, a groove 164, an inlet 163, two nozzles 161a and bristle tufts 161b in the toothbrush head 161. The Waterjet Brush tip 160 further comprises a conduit from the inlet 163 to inside of the tip body 162 then to the lower layer of the toothbrush head 161 then fluidly connects to the nozzles 161a. The nozzles 161a are shaped a narrowed top conical hose. The two nozzles 161a are located at the crosses of the front and the side edges of the toothbrush head 161. The location of nozzles 161a allow user to figure out where is the nozzle 161a during usage. The nozzles 161a are shorter than the bristle tufts 161b to avoid the nozzle to be blocked and ensure the core of the water jet is on user's teeth surface. The bristle tufts 161b are stably support nozzles 161a staying and cleansing a location for a while. For example, user can use nozzle 161a to blast white spot lesion to destroy the white spot lesion's developing environment for couple seconds. This kind of performances were done by a third party using a water jet in a laboratory and removed 99.9% plaque but never achieved by a user. User could also use the nozzles 161a penetrating to dilute the acid for avoid lesion. The nozzles 161a eject water jet to cleansing and the bristles 161b brushing the teeth and interdental simultaneously.

Figure 5:
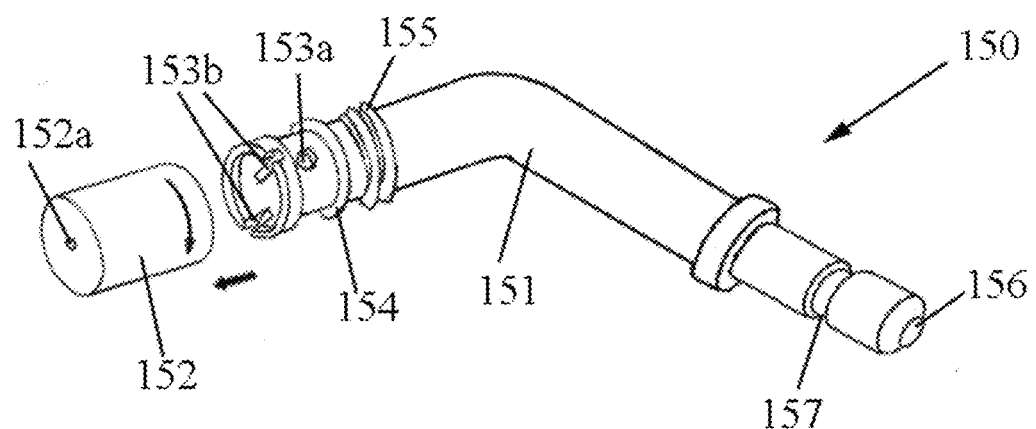
FIG. 5 is a schematic showing an embodiment of tip, a Swirl waterJet tip.

For user who has gum disease a Swirl Waterjet tip 150 is recommended. With reference to FIG. 5, The Swirl Waterjet tip 150 comprises a pipe 151 which has a close off end, a cap 152 with internal thread and a pinhole 152a centrally located at the top of the cap 152, a swirl generator 153a-153b, a ring gasket 154, an external thread 155 that matches internal thread of the cap 152, an inlet 156 and a groove 157. The swirl generator 153a-153b is at the close off end of the pipe 151 and comprises two holes 153a located opposite each other in the side of the pipe 151 and divides a single fluid flow to two. When the cap 152 is screwed onto the pipe 151, the two fluid flows are blocked by the ring gasket 154 then water flows through the two lifting lines 153b which located on the close off end of the pipe 151. For the sake of the clarity the two lifting lines 153b are parallel but do not pass through the center of the close off end of the pipe 151. When the cap 152 is screwed slightly loose against the pipe 151, a water jet stream is ejected out and deep cleans the interdental area. When the cap 152 is screwed tighten against the pipe 151, two water flows twists out from the pinhole 152a to form a high speed rotating umbrella shaped water wheel which opens a user's periodontal pocket to washout plaque therein. The high speed rotating umbrella shaped water wheel also generates a low pressure zone and suck out plaque in deep of user's periodontal pocket.

Figure 7:
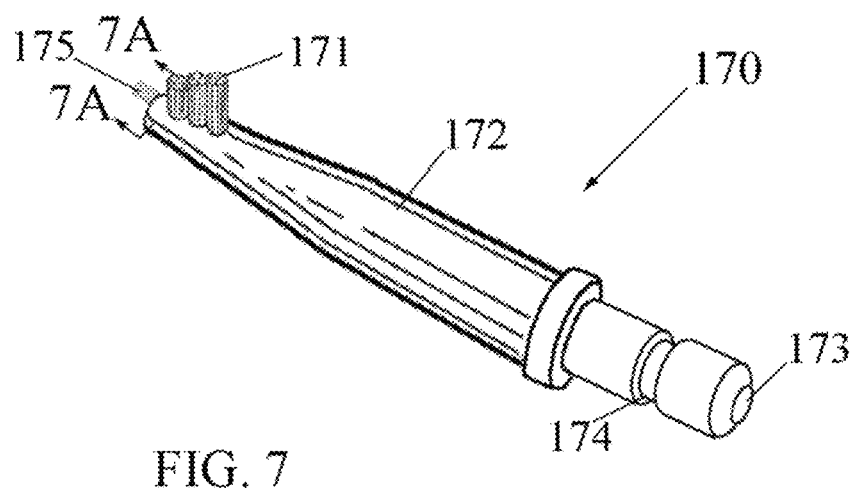
FIG. 7 is a schematic showing an embodiment of tip, a Jet Goupillon tip.
Figures 1, 7:
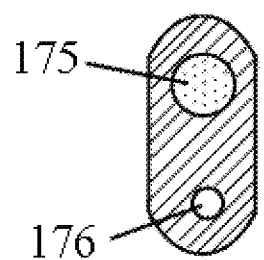

With reference to FIG. 7 and FIG. 7-1, an embodiment of the Jet Goupillon tip 170 comprises a front bristle tuft 175, side bristle tufts 171, a pinhole 176, a tip body 172, a groove 174 and an inlet 173. The Jet Goupillon tip 170 further comprises a conduit from the inlet 173 to inside of the tip body 172 and fluidly connects to the pinhole 176. The layout of the bristles 171 likes a goupillon. The side bristles 171 are gradually shorter forward to front and enable to clean the narrowed portion inside trays or retainers such as Invisalign. The front bristle tuft 175 and side bristle tufts 171 plus water jet from pinhole 176 could clean aligners, retainers, dentures and artificial teeth for orthodontic and dental treatment patients.

Thus, specific embodiments and applications of a compact oral hygiene device have been disclosed. It should be apparent, however, to those skilled in the art that many more modifications beside those already described are possible without departing from the inventive concepts herein. The inventive subject matter, therefore, is not to be restricted except in the spirit of the appended claims. Moreover, in interpreting both the specification and the claims, all terms should be interpreted in the broadest manner possible consistent with the context. In particular, the terms "comprises" and "comprising" should be interpreted as referring to elements, components, or steps in a non-exclusive manner, indicating that the referenced elements, components, or steps may be present or utilized, or combined with other elements, components or steps that are not expressly referenced.

What is claim is:

1. A compact oral hygiene device comprises:
    a body which is housing a mini constant jet pump, a battery and a control circuitry; and
    a detachable reservoir; and
    an oral hygiene-ware comprises a flexible hose, a handle, and a plurality of exchangeable tips;
    wherein said mini constant jet pump integrated with a motor and comprises three diaphragm chambers and a buffer room; said mini constant jet pump further comprises a lever having triple arms with each arm mounted at said three diaphragm chambers respectively; said lever is not rotating during said motor running, but said triple arms are oscillating asynchronously up and down with one of said triple arms is going down causing a volume of the corresponding diaphragm chamber to decrease and to propel fluid out to said buffer room, and simultaneously two other arms are going up causing volumes of the two corresponding diaphragm chambers to increase and to draw fluid from said detachable reservoir into said two corresponding diaphragm chambers, circulation of fluid is repeated during the motor running; and
    said mini constant jet pump propels out a constant pulseless fluid jet from said buffer room.

2. The compact oral hygiene device of claim 1, wherein one of the plurality of exchangeable tips having a pipe with a male external thread and a cap with a female internal thread and a pinhole centrally located at a top end of the cap, an end near the male external thread of said pipe includes a swirl generator that divides single flow into two separated flows then twists said two flows; and
    wherein when said cap is screwed tightly against said pipe, water from the two separated flows twisted and ejected out from said pinhole in a shape that both opens a user's periodontal pocket to wash out plaque therein and to suck out plaque therein and when said cap is screwed loosely against said pipe, water ejected out from the said pinhole in a form of a water stream that cleanses the user's interdental area.

3. The compact oral hygiene device of claim 1, wherein one of the plurality of exchangeable tips having a toothbrush head having two nozzles each located at two side ends respectively of a front edge of said toothbrush head; said nozzles are shaped as narrowed top conical hoses; said nozzles are shorter than bristles of said toothbrush head to avoid the nozzles to be blocked and to ensure the fluid jet's core is on user's teeth surface and to blast white spot lesion to stop tooth decay process; said tip is used for water jet cleansing and bristles brushing simultaneously.

4. The compact oral hygiene device of claim 1, wherein one of the plurality of exchangeable tips having a syringe-brush at a front end; said syringe-brush comprises bristles that are gradually shorter forward to the front end and enable to clean narrowed portion inside dental trays or retainers; said tip further comprises a pinhole in the front end of said tip to eject fluid; said tip cleanses dental aligners, retainers, dentures and artificial teeth for orthodontic and dental treatment patients.

* * * * *